United States Patent
Germini et al.

(10) Patent No.: US 8,908,168 B2
(45) Date of Patent: Dec. 9, 2014

(54) SYSTEMS AND METHODS FOR THE ANGULAR ORIENTATION AND DETECTION OF CONTAINERS IN LABELLING MACHINES

(75) Inventors: Fabrizio Germini, Parma (IT); Antonio Secchi, Parma (IT)

(73) Assignee: Sidel S.p.A., Parma (IT)

( * ) Notice: Subject to any disclaimer, the term of this patent is extended or adjusted under 35 U.S.C. 154(b) by 382 days.

(21) Appl. No.: 13/388,963

(22) PCT Filed: Aug. 5, 2009

(86) PCT No.: PCT/IB2009/053404
§ 371 (c)(1),
(2), (4) Date: Mar. 1, 2012

(87) PCT Pub. No.: WO2011/015899
PCT Pub. Date: Feb. 10, 2011

(65) Prior Publication Data
US 2012/0147360 A1    Jun. 14, 2012

(51) Int. Cl.
*G01B 11/26* (2006.01)
*B65C 9/06* (2006.01)

(52) U.S. Cl.
CPC ...................................... *B65C 9/067* (2013.01)
USPC ......................................................... 356/138

(58) Field of Classification Search
CPC .................. G01N 21/9045; G01N 2021/8924; G01N 2021/8965; B65C 9/067
USPC .................. 356/138–153, 614–624
See application file for complete search history.

(56) References Cited

U.S. PATENT DOCUMENTS

| | | | |
|---|---|---|---|
| 3,411,625 A * | 11/1968 | Calhoun | 209/524 |
| 3,891,324 A * | 6/1975 | Davies | 356/615 |
| 4,655,548 A * | 4/1987 | Jue | 348/373 |
| 4,691,231 A * | 9/1987 | Fitzmorris et al. | 348/127 |
| 5,443,164 A * | 8/1995 | Walsh et al. | 209/580 |
| 5,831,738 A * | 11/1998 | Hine | 356/399 |
| 5,991,018 A * | 11/1999 | Imaizumi et al. | 356/239.1 |
| 6,953,262 B2 * | 10/2005 | Cleaver et al. | 362/219 |
| 7,331,152 B2 * | 2/2008 | Menke | 53/67 |
| 8,477,185 B2 * | 7/2013 | Secchi et al. | 348/86 |
| 2010/0141756 A1 * | 6/2010 | Grote et al. | 348/127 |
| 2010/0289890 A1 * | 11/2010 | Niedermeier et al. | 348/95 |
| 2010/0290695 A1 * | 11/2010 | Kwirandt | 382/142 |
| 2011/0140010 A1 * | 6/2011 | Akkerman et al. | 250/553 |

FOREIGN PATENT DOCUMENTS

| | | |
|---|---|---|
| DE | 102005041497 | 3/2007 |
| EP | 1298428 | 4/2003 |
| EP | 1510809 | 3/2005 |
| EP | 1777163 | 4/2007 |

(Continued)

OTHER PUBLICATIONS

International Search Report, dated May 7, 2010 (completed), pp. 1-4.

*Primary Examiner* — Michael A Lyons
*Assistant Examiner* — Shawn Decenzo
(74) *Attorney, Agent, or Firm* — Tarter Krinsky & Drogin LLP

(57) ABSTRACT

Systems and methods for the angular orientation and detection of containers being processed in labeling machines are provided. An apparatus is provided comprising a rotating turntable, a plurality of motor-driven pans each having a controller, an optical sensor and an illuminating device. Also discussed are methods for the detection and angular orientation of containers in labeling machines with such an apparatus.

13 Claims, 4 Drawing Sheets

(56) References Cited

FOREIGN PATENT DOCUMENTS

| | | |
|---|---|---|
| GB | 2334576 | 8/1999 |
| JP | 2001050898 | 2/2001 |
| WO | 2008072070 | 6/2008 |
| WO | 2009/072157 | 6/2009 |

* cited by examiner

SYSTEMS AND METHODS FOR THE ANGULAR ORIENTATION AND DETECTION OF CONTAINERS IN LABELLING MACHINES

CROSS-REFERENCE TO RELATED APPLICATIONS

This application is a National Phase Application of PCT International Application No. PCT/IB2009/053404, International Filing Date, 5 Aug. 2009, which is hereby incorporated by reference in its entirety.

FIELD OF THE INVENTION

The present invention relates to a system for the angular orientation and detection of containers being processed in labeling machines.

BACKGROUND OF THE INVENTION

The labeling operation of containers in high speed automatic labeling machines sets out the problem of the correct positioning of the label. Such machines usually comprise turntables, on which a plurality of pans is mounted, which are intended to support and handle the containers to be labeled, together with jacks engaging the container upper end in order to hold it in an upright position on the pan. Such pans are motor-driven, so as to allow the rotation thereof and of the containers they support around the vertical axis thereof. This operation serves to the label application, which label will thus wrap around the container side surface during the rotation thereof.

In a machine as the one described herein, which operates at a high speed, the container angular orientation according to a preset pattern is critical for a smooth operation of the machine.

In the conventional plants, the container correct orientation is achieved by a timing of a mechanical type which, however, often turns out to be not very reliable.

In labeling machines for glass containers, systems have been proposed wherein one or more cameras are positioned along the path of the carrousel in order to read an indentation or other marks such as wrinkles or dots that are present on a bottom area of the container. These systems also comprise a computing and control unit that elaborates the images taken by the one or more cameras, makes a comparison between such images and a reference image or a calibration graph and finally controls the rotational position of the containers on the supporting pans, so that the containers are all oriented the same way.

One critical issue in these systems is the reliability of identification of such indentation or marks present on the containers. Errors in the identification of such marks would result in an erroneous re-positioning of the container and thus in an unreliable labeling operation.

SUMMARY OF THE INVENTION

The angular orientation and detection system of the containers being the object of the invention, as set forth in the annexed claims, the contents of which are an integral part of the present description, allows a reliable identification of the marks present on the container, thus greatly improving the efficacy of the re-orientation system of the invention.

It has been seen that such a result can be achieved by means of a specific positioning of the illumination system with respect to the containers and to the camera system.

Further characteristics and the advantages of the present invention will be more clearly understood from the description of an exemplary embodiment, given herein below by way of illustrative and non-limiting example, with reference to the following Figures:

DETAILED DESCRIPTION

Figure 1:
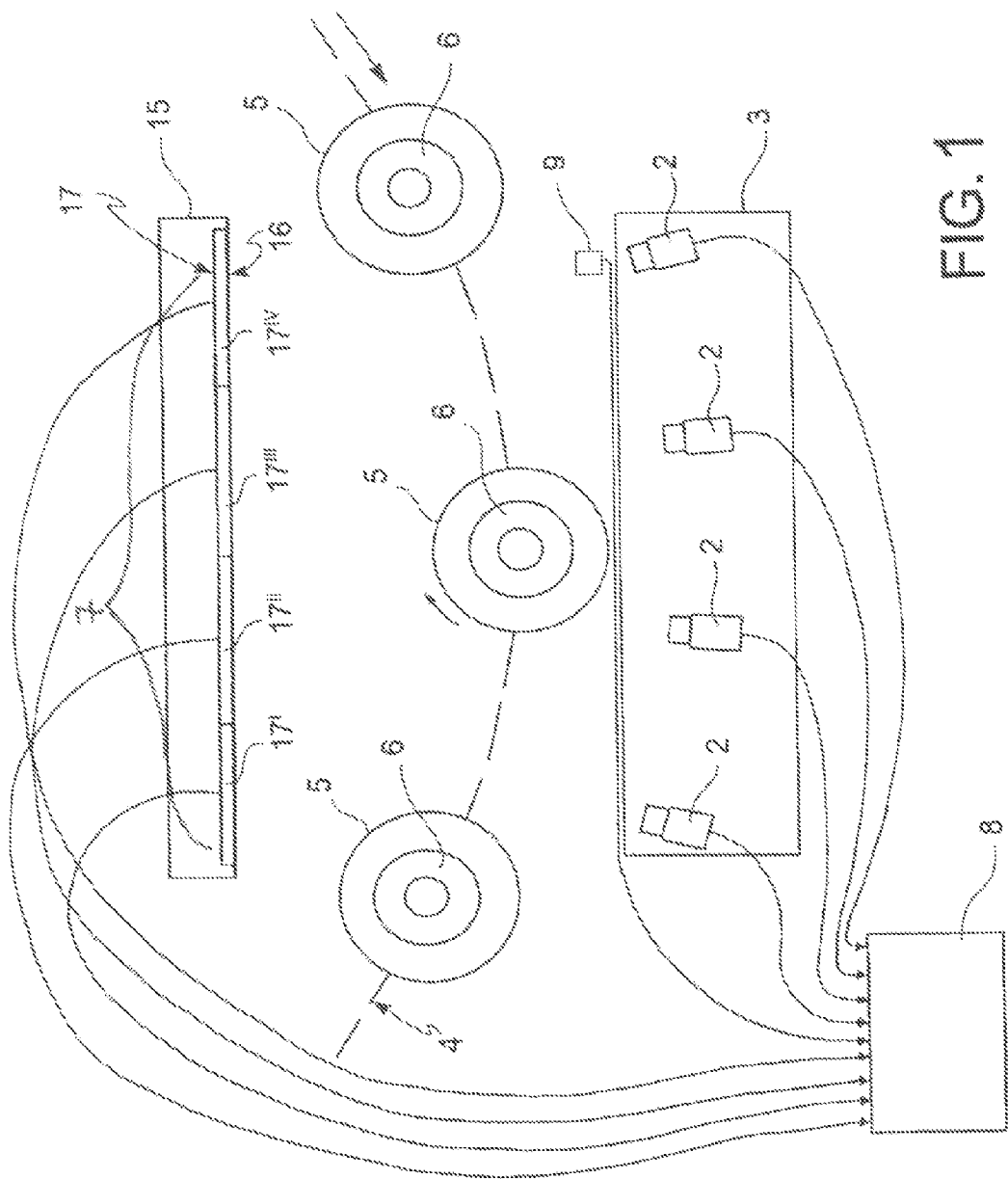
FIG. 1 represents a schematic top view of the system which is the object of the invention.

With reference to the Figures, the orientation and detection system of the containers of the invention will be now described, generally indicated with the reference numeral 1.

In general, the containers that can be processed in the inventive system are transparent or translucent containers, such containers in glass or plastics.

The system 1 comprises four optical sensing means 2, such as a camera for image acquisition. However, in different embodiments, only one optical sensing means 2 can be used, such as in the case wherein the containers have a symmetrical shape that can be easily detected by the vision system without the need of specific marks or indentations. One example may be a container with polygonal cross section. Thus, according to specific needs, one or more optical sensing means 2 can be used. When the containers have the typical reference marks, such as dots or the like positioned in the lower portion of the container side, the embodiment described below with four optical sensing means 2 allows the system 1 to take a complete picture of the container side, as will be explained thereafter.

In general, the term "reference mark" as used in the present invention should intended as dots, wrinkles, embossing or the like positioned in any suitable portion of the container, such as the lower side portion or the neck portion, as well as the same edges or other raised areas of the container, as explained above.

Such optical sensing means 2 are housed within a housing 3, preferably made of metallic material, but having walls of a transparent material, preferably anti-burglary glasses, at least at the optical sensing means 2 visual field.

The housing 3 is arranged externally relative to a turntable 4 for the handling of containers, and the optical sensing means 2 contained therein are orientated along an arc of circle having essentially the same radius of curvature as the turntable 4. The rotating turntable 4 is a conventional turntable of the type having a plurality of motor-driven pans 5 which support and handle the containers 6.

Suitable illuminating means 7 are located in front of the said optical sensing means 2, internally with respect to the turntable 4, so that the containers 6 pass between the said optical sensing means 2 and the said illuminating means 7. It is also possible to invert the position of the optical sensing means 2 and of the illuminating means 7, so that these latter are positioned externally and the means 2 are positioned internally with respect to the turntable 4.

Moreover, while the optical sensing means 2 visual field intercepts at least a portion of the container 6 passing therebetween, namely the container 6 portion wherein the reference marks are present, the said illuminating means 7 are positioned on a substantially vertically translated plane therefrom. In such a way, the containers 6 are subject to a backlight inclined illumination which emphasises any reference sign in relief that is present on the container.

In general, therefore, it can be said that the optical sensing means 2 and the illuminating means 7 must be positioned in different radial configurations in such a way that one of them is positioned externally and the other one is positioned internally with respect to the turntable 4, and that the illuminating means 7 must lie on a substantially vertically translated plane with respect to the plane of the optical sensing means 2.

Preferably, the optical sensing means 2 are external and the illuminating means are internal to the turntable 4 and the illuminating means 7 lie on a plane above the plane of the means 2.

The said illuminating means 7 are contained in a housing 15 having a front surface 16 made of a translucent material, so that the light is uniformly diffused therefrom.

In one embodiment, the said illuminating means 7 are white led bar illuminators 17. For example, a led bar of about 600 mm length can be used.

In one embodiment, the said led bar is made of a plurality of led bars 17', 17", 17''', 17$^{iv}$ one for each optical sensing means 2—operatively linked together.

A photocell 9 is arranged in alignment with the visual axis of an optical sensing means 2, in an overhead position relative to the container 6. Such photocell 9 reads the presence of the container in the correct position by intercepting the upper jack for the setting of the same container.

If more than one optical sensing means 2 is provided, the said photocell 9 can be located for example at the first optical sensing means 2 in the direction of the rotation of the turntable 4, or in any other optical sensing means 2.

The optical sensing means 2, the respective illuminating means 7 and the photocell 9 are operatively connected—by suitable wiring, as in the exemplary figure, or by wireless systems to a computing and control unit 8 which, through suitable software, provides for the system actuation as described below.

Figure 3:
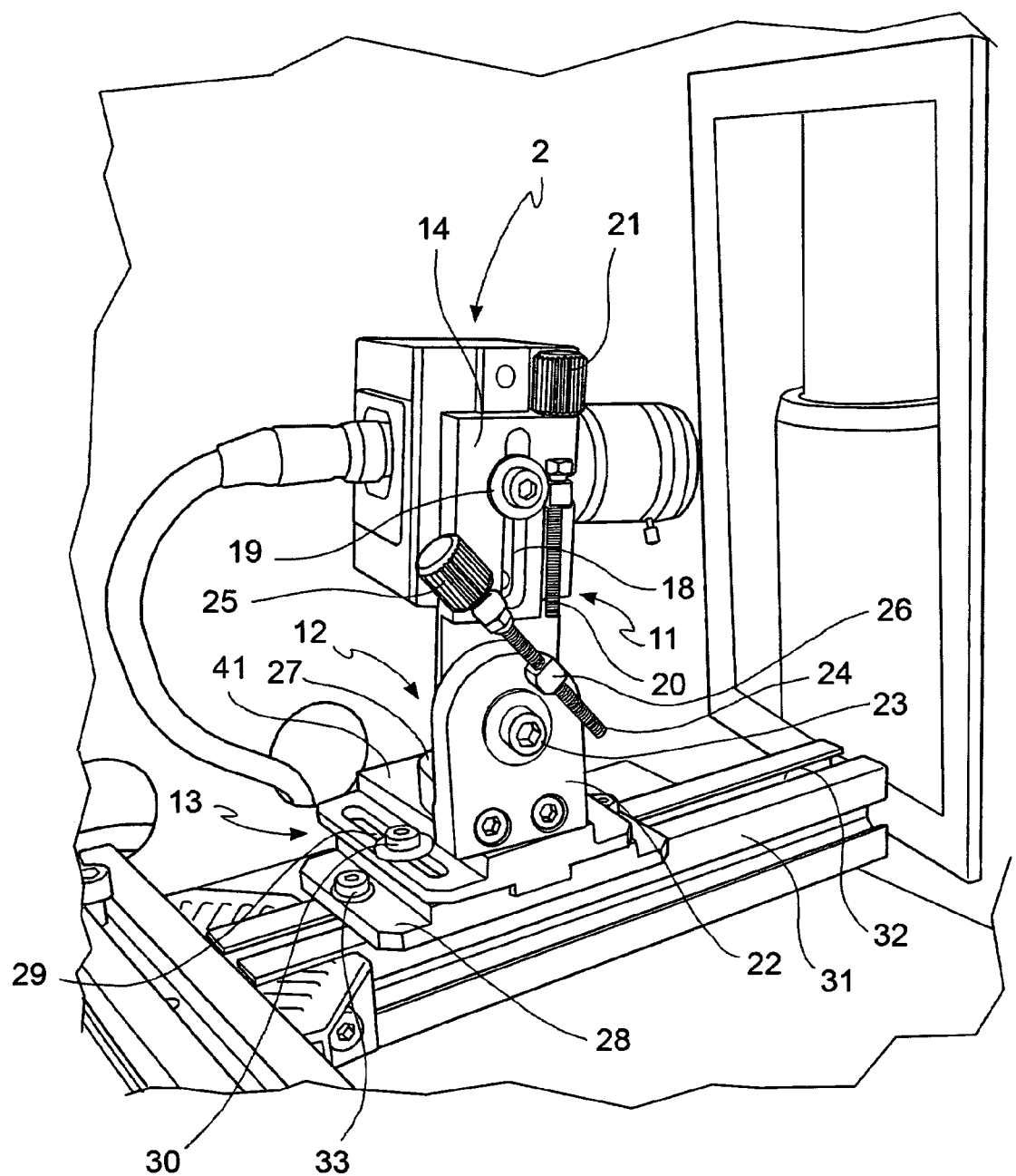
FIG. 3 represents a perspective view of a detail of the system of FIG. 2.
Figure 4:
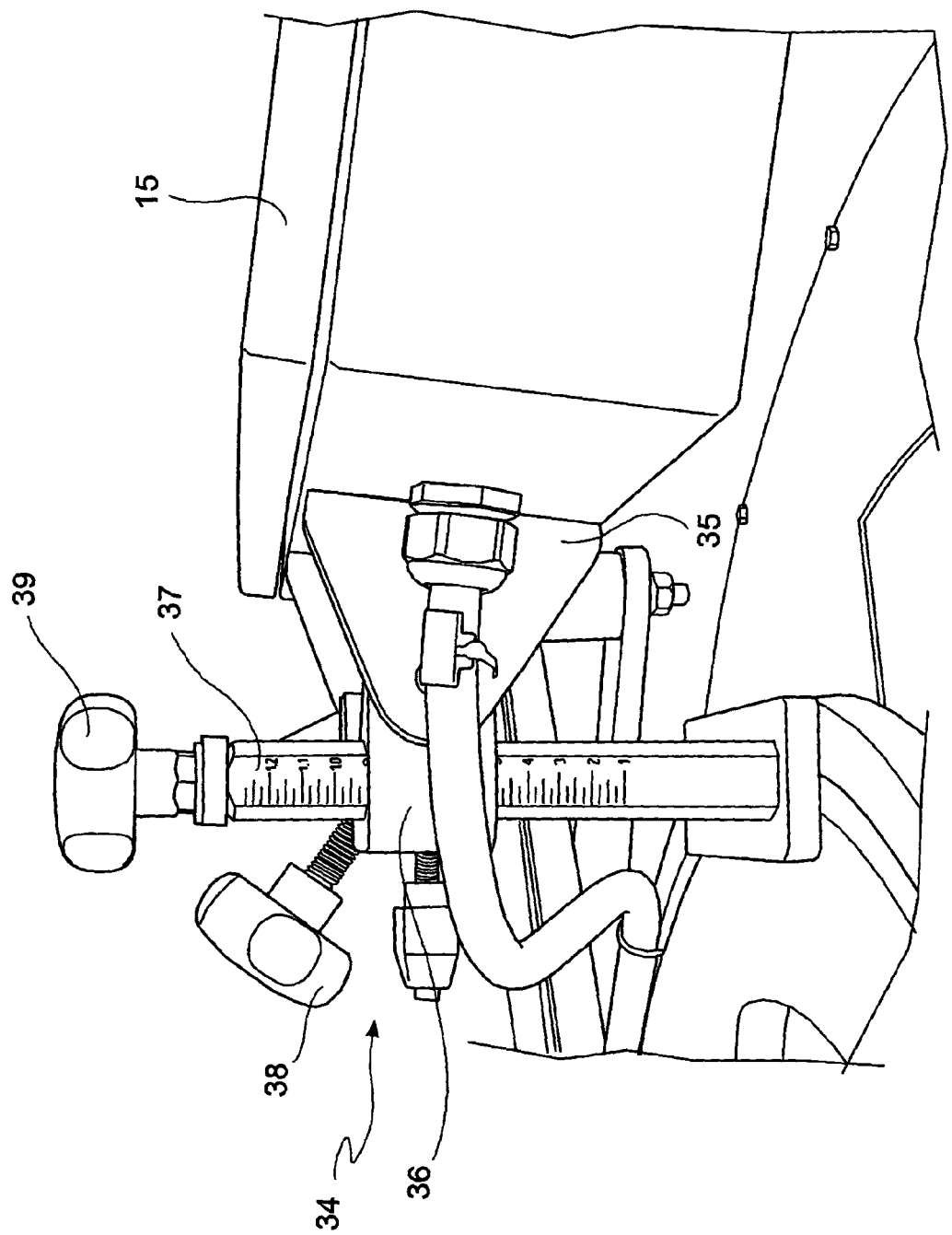
FIG. 4 represents a perspective view of another particular of the system of FIG. 2.

As shown in FIG. 3, the optical sensing means 2 are mounted on adjustable supports 10. The supports 10 comprise adjustment means 11 for the top-down vertical adjustment of the means 2; adjustment means 12 for the horizontally pivoted top-down and side-by-side adjustment of the means 2; and adjustment means 13 for the lateral adjustment, as well as for the forward-backward translation. In this manner, it is possible to achieve a fine adjustment of the optical sensing means 2 position, thus the correct aiming of the container 6. Such initial aiming is extremely important, since it dictates the system 1 operation. The system software provides reference elements which allow framing the container 6 and adjusting the optical sensing means 2 so as to align the system reference elements to the reference marks which are present on the container.

The adjustment means 11 comprise a supporting bar 14 having a vertical elongated slot 18, wherein holding and guiding means 19 are inserted in order to hold the optical sensing means 2 in the desired vertical position. An adjusting screw 20 is associated to the optical sensing means 2 and passes through a vertical threaded hole in the supporting bar 14 top. The adjusting screw 20 has a corrugated head 21 serving as a handling means. By screwing or unscrewing the said adjusting screw 20 it is possible to lower or raise the optical sensing means 2, thus providing a vertical adjustment.

The adjustment means 12 comprise a plate 22 that is hinged by hinging means 23 to the support bar 14. An adjusting screw 24, having a corrugated head 25 serving as a handling means, is associated to the supporting bar 14 and passes through an internally threaded sleeve 26 fixed to the plate 22. The adjusting screw 24 is inclined with respect to the vertical, so that by screwing or unscrewing it is possible to pivot the supporting bar 14—and thus the optical sensing means 2 associated thereto—in a top-down arrangement. This allows to adjust the inclination of the optical sensing means 2 with respect to the visual field.

Figure 2:
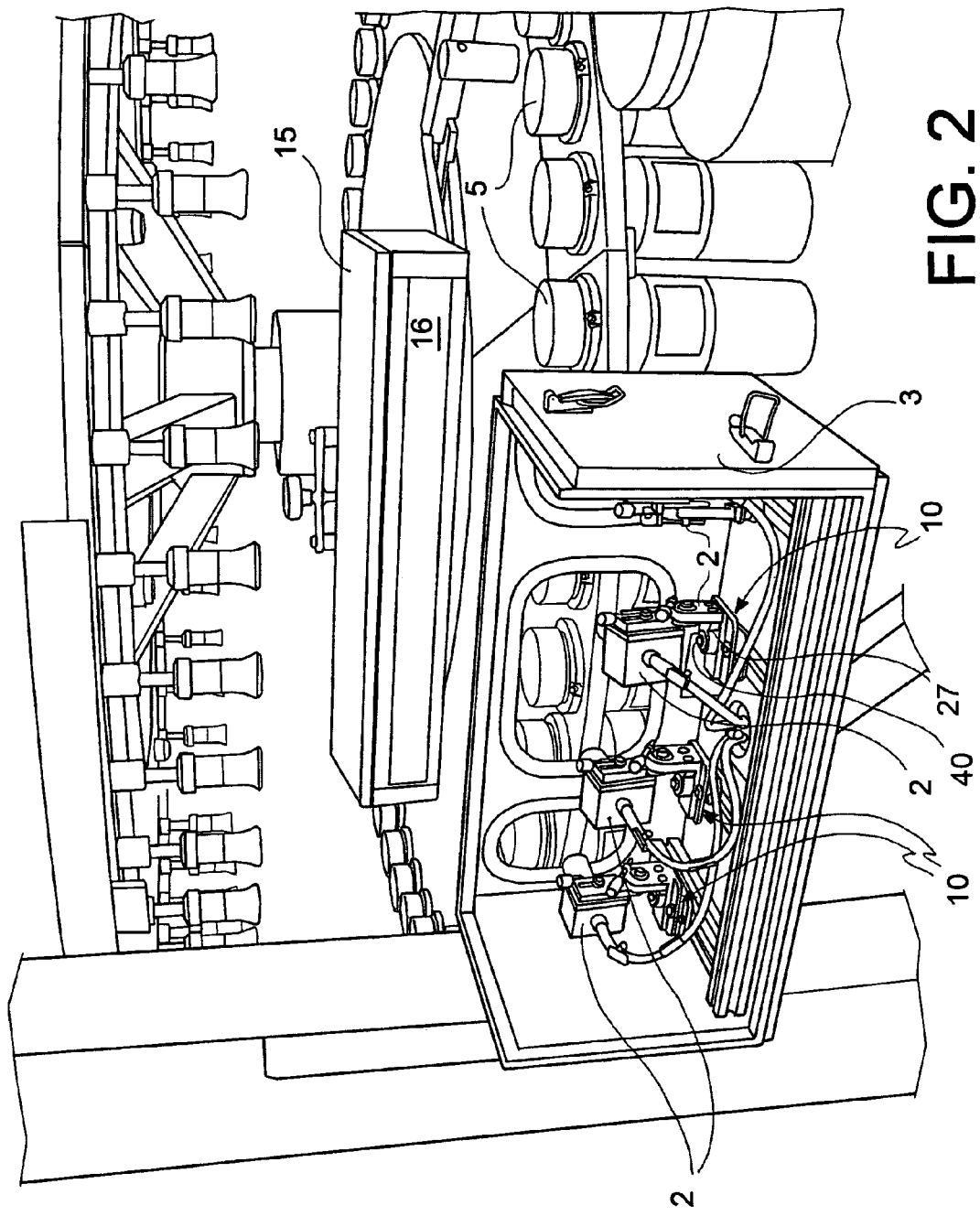
FIG. 2 represents a perspective view of the system of FIG. 1.

The plate 22 is fixed to or integral with a base element 27, so that they form an L-shaped element. Holding means 40 (see FIG. 2) are provided, wherein, by loosening such holding means 40, it is possible to pivot the adjustment means 12 side-by-side around an horizontal axis, that is substantially radial with respect to the turntable 4.

The adjustment means 13 comprise a first base plate 41. The said first base plate 41 is mounted in a sliding arrangement on a second base plate 28 to allow the lateral movement of the support 10. To this end, the first base plate 41 is provided with an elongated slot 29 wherein holding and guiding means 30 are inserted. By loosening this holding and guiding means 30, it is possible to slide laterally the first base plate 41 with respect to the second base plate 28. A second slot-holding and guiding means assembly may be provided at an opposite end of the first base plate 41, in order to provide a better guide to the support 10.

On its turn, the second base plate 28 is mounted in a sliding arrangement on a bar 31, that is positioned along a substantially radial direction with respect to the turntable 4. The bar 31 comprises a C-shaped groove 32 wherein holding and guiding means 33 for the second base plate 28 are inserted and operatively associated thereto, so that, by loosening said holding and guiding means 33, the second base plate 28—and thus the whole support 10—can slide forward or backward with respect to the turntable. This allows the adjustment of the visual field of the optical sensing means 2.

The housing 3 as a whole can also be adjusted vertically and/or laterally along suitable guiding means not shown, in order to allow a rough adjustment of the optical sensing means position, while the fine adjustment thereof is provided by the adjustable support 10 as explained above. This rough adjustment is also very important, as it allows to adapt the system to different container sizes and typologies.

The illuminating means 7 are also adjustable to orient them in a proper way with respect to the container to be illuminated.

The housing 15 is mounted on an adjustable support 34 that allows the top-down horizontally pivoting adjustment and the vertical adjustment thereof.

In more details, a connecting element 35 is fixed to or is integral with the housing 15, typically at the back thereof. This connecting element 35 can be made of one or more plates protruding from the back of the housing 15.

The connecting element 35 is hinged to a slidable support 36 moving up and down along a rod 37.

Both the pivoting movement of the connecting element 35 and the vertical movement of the slidable support 36 are regulated by adjusting means 38, 39, respectively, for example of the type above described in relation to the adjustment means of the support 10 for the optical sensing means 2.

The orientation of the illuminating means 7 with respect to the container to be illuminated is important in order to provide an inclined illumination of the raised dots or other reference marks on the container. In such a way, the contrast in the image taken by the optical sensing means 2 is maximised.

Both the adjustment means 11, 12, 13 of the support 10 and the adjustable support 34 of the illuminating means 7 may be provided with suitable scale marks, to allow precise and repeatable setting of the system.

The above-described system works as follows.

As said above, the containers have reference marks which can be composed of a series of wrinkles or dots in the proximity of the bottom, or writings, or other indicia. Such reference marks are then used for the correct orientation of the container on the pan. The containers arrive on the several pans in a completely random angular position, therefore a re-orientation thereof is required, i.e. it is necessary to angularly orientating all of them in the same position before they reach the labeling step.

In one embodiment, the four optical sensing means 2 are adapted to take an image of the bottle throughout side surface. More precisely, four images will be taken for each container, one for each means 2. The set of four images relative to each container is analyzed by the computing and control unit 8 as explained below.

In another embodiment, only one optical sensing means 2 is present, so that only one image will be taken for each container. This is the case wherein the container presents a repeating reference mark such as the edges of a container with regular polygonal cross section.

In any case, the system 1 will perform the following stages:
  a) Acquiring a set of images of the container under examination;
  b) Identifying the reference marks on the container under examination;
  c) Comparing the set of acquired images to a control set or calibration table;
  d) Calculating the deviation of said reference marks in the container under examination relative to said control set or calibration table;
  e) Sending a command to the controller of the motor of the pan which supports the container under examination, so as to rotate said pan by an angle to accommodate said container position to the reference position.

The said set of images may be composed of only one image or of more than one image, such as four images, according to the number of optical sensing means 2 which the system 1 is endowed with.

The stage a) of image acquisition comprises acquiring at the same time an image of a number of containers corresponding to the number of optical sensing means 2 of the system 1. In the example wherein four optical sensing means 2 are provided, an image of four containers 6 on the turntable is contemporaneously taken. As the turntable 4 rotates, when a new container 6 passes through the first optical sensing means 2 visual field, a new command of image acquisition is sent by the computing and control unit 8: in this way, the container that was first at the previous shot is now arrived at the second optical sensing means 2, the second container to the third optical sensing means 2 and the third to the four. While passing from one optical sensing means 2 to the subsequent one, the pan 5 supporting a container is rotated of 90°, so that when a container passes from the first optical sensing means 2 to the fourth one it has been rotated of 360° and four images thereof have been acquired.

If a different number of optical sensing means 2 is provided, such as two or three, each container will be rotated, passing from an optical sensing means to the subsequent one, of an angle of 360°/n, wherein n is the number of optical sensing means 2 of the system 1. A total of n images for each container are acquired.

The stage a) of image acquisition thus comprises the following steps:
  A1) sending an image acquisition command to the said optical sensing means 2 following the container presence signal by the photocell 9;
  A2) concomitantly, sending a turn on command to the illuminating means 7;
  A3) rotating the pan 5 which supports the container 6 under examination by 360°/n, wherein n is the number of optical sensing means 2;
  A4) repeating the steps A1) and A2) with the subsequent container 6;
  A5) repeating the steps A3) and A4), according to a preset temporal sequence until the acquisition of n images of the container under examination, wherein n is the number of optical sensing means 2.

The software of the system 1 according to the invention allows tailoring to any container formats, through said calibration table, which is created during a suitable calibration step, comprising:
  i) Detecting the already-labeled container diameter and edges, the reference marks which are present on the container, and the image light/dark contrast;
  ii) Acquiring a first set of images of the container being tested, one for each optical sensing means 2;
  iii) Rotating the pan with the container being tested by an angle α, preferably 10° or less, and acquiring a second set of images, one for each optical sensing means 2;
  iv) Repeating the operation of the step iii) a number of times until completing a 360° rotation of the container being tested;
  v) Calculating, for each of them, the distance X between the container edge and reference mark, and associating the corresponding rotation angle to said distance X;
  vi) Creating a calibration table from such data.

The advantages of the angular orientation and detection system of containers according to the invention are clearly understood by those skilled in the art, and can be summarized in a considerable adjustment accuracy (accuracy of the order of 1 mm or less), implementation easiness, and installation and maintenance economy.

More in particular, the illuminating system adopted in the invention allows the contrast in the acquired images to be maximised, thus improving the correctness of the reference marks identification and minimizing the likelihood of errors.

It shall be understood that only some particular embodiments of the present invention have been described, to which those skilled in the art will be able to make all the required modifications for the accommodation thereof to particular applications, without anyhow departing from the scope of protection of the present invention.

For example, the illumination means 7 may be replaced by an X-ray emitting source and the optical sensing means 2 by sensing means apt to acquire an X-ray image. In this embodiment, the containers may also be opaque to the light, as the X-ray beam can pass through the containers body, providing a sort of "backlight inclined illumination" as described above.

The invention claimed is:
1. An apparatus for the detection and angular orientation of containers in labelling machines comprising,
a rotating turntable for the handling of containers, said turntable defining a radius of curvature, a plurality of motor-driven pans each having a controller, said motor-driven pans being rotatably connected to said rotating turntable for supporting said containers, an optical sensor lying along a horizontal plane, said optical sensor positioned external to the rotating turntable and oriented along an arc of a circle having a radius corresponding to said radius of curvature of said turntable, said sensor being adapted for acquiring an image of one or more container rotated on said motor-driven pans, first adjustment means for selectively adjusting the height of said optical sensor relative to the height of the turntable, an illuminating device positioned internally with respect to said turntable such that each container, when supported by a motor-driven pan, passes between said optical sensor and said illuminating device, said illuminating device positioned above said horizontal plane on which said optical sensor lies, such that said illuminating device is capable of providing high-contrast inclined-backlighting illumination of said containers, for maximizing contrast of any reference sign present on said containers, second adjustment means for selectively adjusting the height and orientation of said illuminating device, a photocell arranged in alignment with said optical sensor, said photocell being adapted for detecting the presence or absence of a container on each of said motor-driven pans, said first and second adjustment means being adjustable for placing said photocell in alignment with said optical sensor in a manner that optimizes image contrast, a computing and control unit operatively connected to said optical sensor, illuminating device and photocell; said computing and control unit capable of acquiring images, identifying reference signs on containers, comparing the reference signs to a calibration table, calculating deviation from the calibration table, and sending a command to one or more controllers of said motor-driven pans to rotate said motor-driven pan to correct said deviation.

2. The apparatus of claim 1, wherein the optical sensor is external and the illuminating device is internal to the turntable and the illuminating device lies on a plane above the plane of the optical sensor.

3. The apparatus of claim 1, wherein the containers are at least partially transparent or translucent and are subject to a backlight inclined illumination.

4. The apparatus of claim 1, wherein the optical sensor is orientated along an arc of circle having the same radius of curvature as the turntable.

5. The apparatus of claim 1, wherein the illuminating device comprises white light emitting diode (LED) bar illuminators.

6. The apparatus of claim 5, wherein the light emitting diode (LED) bar illuminators comprise a plurality of light emitting diode (LED) bars, each associated with an optical sensor and operatively linked with one another.

7. The apparatus of claim 1, wherein the optical sensor is mounted on adjustable supports comprising, adjustment means for the top-down vertical adjustment of the optical sensor, adjustment means for the horizontally pivoted top-down and side-by-side adjustment of the optical sensor, and adjustment means for the lateral adjustment, as well as for the forward-backward translation of the optical sensor.

8. The apparatus of claim 7, wherein the adjustment means comprise a first base plate, the first base plate being mounted in a sliding arrangement on a second base plate to allow the lateral movement of the support.

9. The apparatus of claim 7, wherein the adjustment means comprise scale marks.

10. A method for the detection and angular orientation of containers in labelling machines with the apparatus of claim 1, wherein said computing and control unit perform the steps of:

acquiring a set of images of the container under examination;

identifying the reference marks on the container under examination; comparing the set of acquired images to a control set or calibration table;

calculating the deviation of said reference marks in the container under examination relative to said control set or calibration table; and sending a command to the controller of the motor of the pan which supports the container under examination, so as to rotate said pan by an angle to accommodate said container position to the reference position.

11. The method of claim 10, wherein the step of acquiring a set of images comprises:

A1) sending an image acquisition command to the optical sensor following the container presence signal by the photocell;

A2) concomitantly, sending a turn-on command to the illuminating device;

A3) rotating the pan which supports the container under examination by 360°/n, wherein n is the number of optical sensors;

A4) repeating the steps A1) and A2) with a subsequent container; and

A5) repeating the steps A3) and A4), according to a preset temporal sequence until the acquisition of n images of the container under examination, wherein n is the number of optical sensors.

12. The method of claim 10, wherein the calibration table is obtained according to the following steps:

i) detecting the already-labelled container diameter and edges, the reference marks which are present on the container, and the image light/dark contrast;

ii) acquiring a first set of images of the container being tested, one for each optical sensor;

iii) rotating the pan with container being tested by an angle α, and acquiring a second set of images, one for each optical sensor;

iv) repeating the operation of step iii) until completing a 360° rotation of the container being tested;

v) calculating, for each of them, the distance X between the container edge and reference mark, and associating the corresponding rotation angle to said distance X; and vi) creating a calibration table from such data.

13. The apparatus of claim 1, comprising four optical sensors.

* * * * *